United States Patent
Johnsen

(10) Patent No.: US 8,439,883 B1
(45) Date of Patent: May 14, 2013

(54) REPOSITIONABLE POUCH WITH FLOATING LANDING ZONE

(75) Inventor: Kenneth A. Johnsen, Piscataway, NJ (US)

(73) Assignee: Convatec Technologies, Inc., Reno, NV (US)

( * ) Notice: Subject to any disclaimer, the term of this patent is extended or adjusted under 35 U.S.C. 154(b) by 0 days.

(21) Appl. No.: 09/196,071

(22) Filed: Nov. 19, 1998

Related U.S. Application Data

(60) Provisional application No. 60/066,276, filed on Nov. 20, 1997.

(51) Int. Cl.
*A61F 5/44* (2006.01)
(52) U.S. Cl.
USPC ............ 604/338; 604/339; 604/342; 604/344
(58) Field of Classification Search ........... 604/332–344
See application file for complete search history.

(56) References Cited

U.S. PATENT DOCUMENTS

| | | | | |
|---|---|---|---|---|
| 4,701,169 A | * | 10/1987 | Steer | 604/344 |
| 4,894,058 A | * | 1/1990 | Jensen | 604/332 |
| 5,074,852 A | * | 12/1991 | Castellana et al. | 604/336 |
| 5,160,330 A | * | 11/1992 | Cross | 604/339 |
| 5,346,482 A | * | 9/1994 | Metz et al. | 604/338 |
| 5,403,299 A | * | 4/1995 | Schneider | 604/332 |
| 5,496,296 A | * | 3/1996 | Holmberg | 604/336 |
| 5,722,965 A | * | 3/1998 | Kuczynski | 604/344 |
| 5,800,415 A | * | 9/1998 | Olsen | 604/336 |
| 6,764,474 B2 | * | 7/2004 | Nielsen et al. | 604/344 |

FOREIGN PATENT DOCUMENTS

| | | |
|---|---|---|
| JP | 9-94299 | 4/1997 |
| JP | 10-192318 | 7/1998 |

* cited by examiner

*Primary Examiner* — Lynne Anderson

(57) ABSTRACT

The ostomy system includes a pouch that is adhesively coupled to a mounting wafer. The mounting wafer has a landing zone film formed of releasable plastic and the pouch has a face plate with a resealable adhesive that secures to the landing zone of the mounting wafer. The landing zone of the mounting wafer includes one portion that is immovable with respect to the body surface that the mounting wafer is secured to and another portion that is deflectable away from the body surface. The deflectable portion of the landing zone, also referred to as the floating landing zone, is sized for gripping between the fingers during pouch separation from the mounting wafer. Gripping of the floating landing zone during pouch separation helps isolate the pouch separation force from the abdominal area underlying the mounting wafer. The mounting wafer also includes indicia border lines that facilitate alignment of the pouch face plate with the mounting wafer.

14 Claims, 6 Drawing Sheets

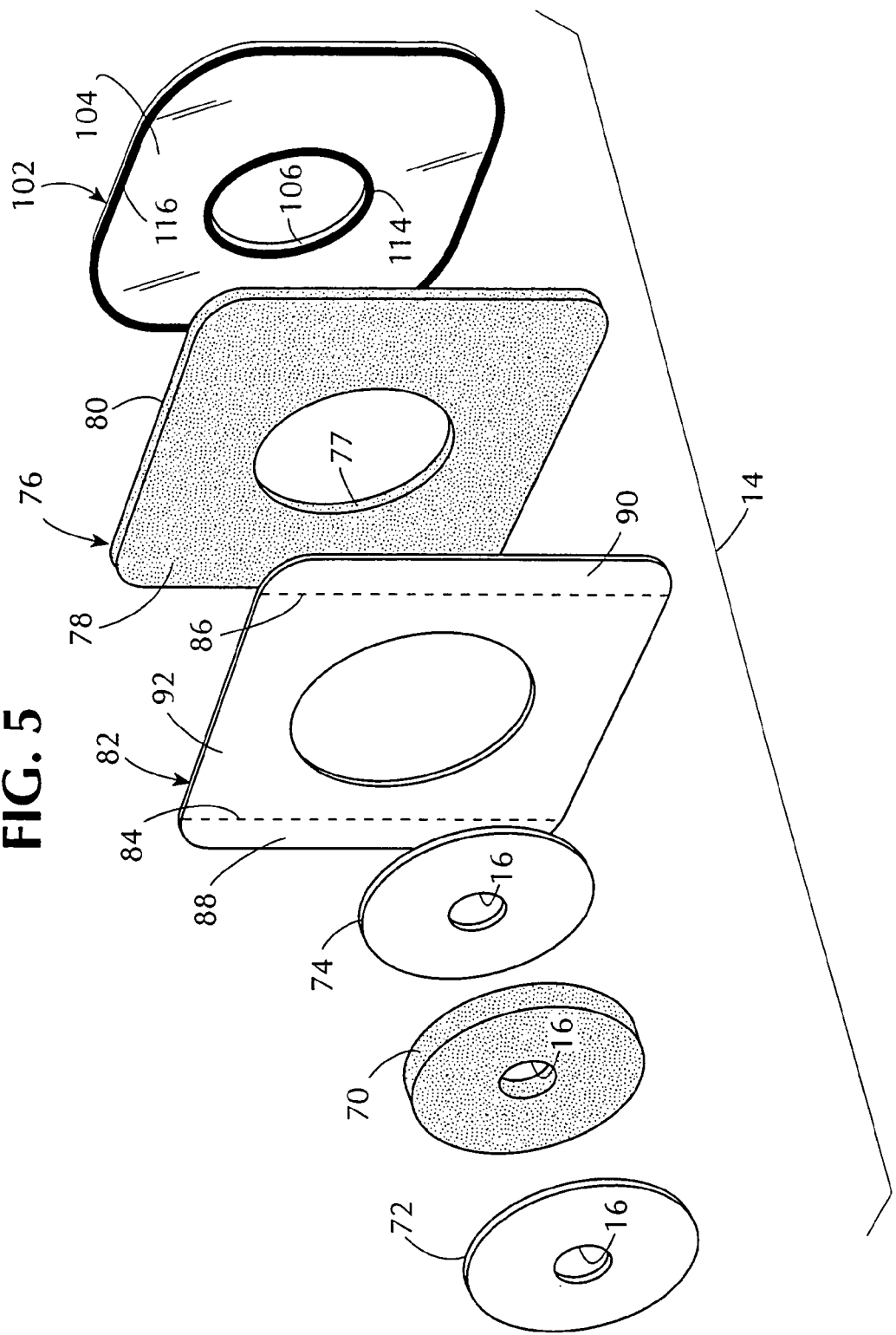

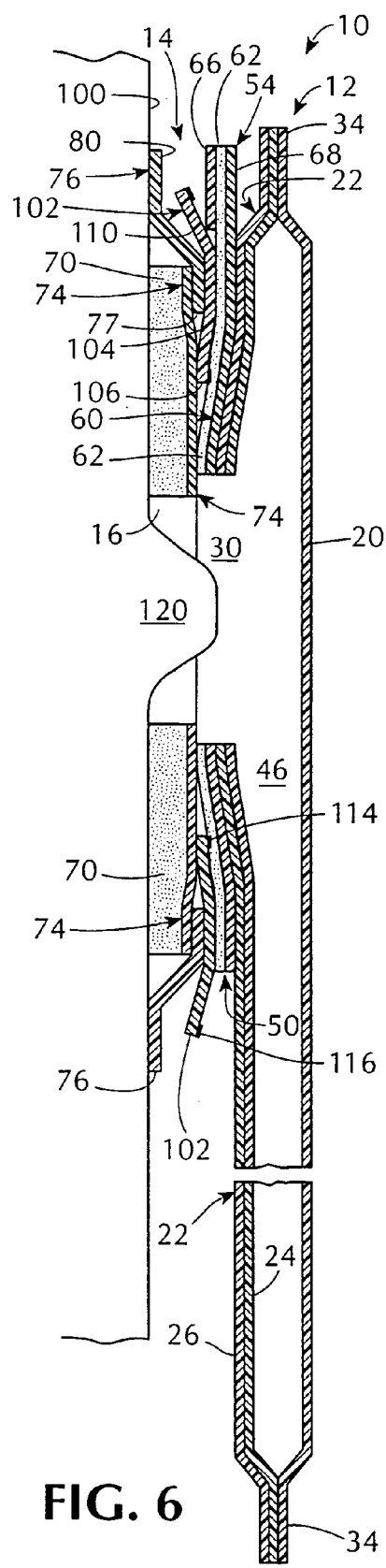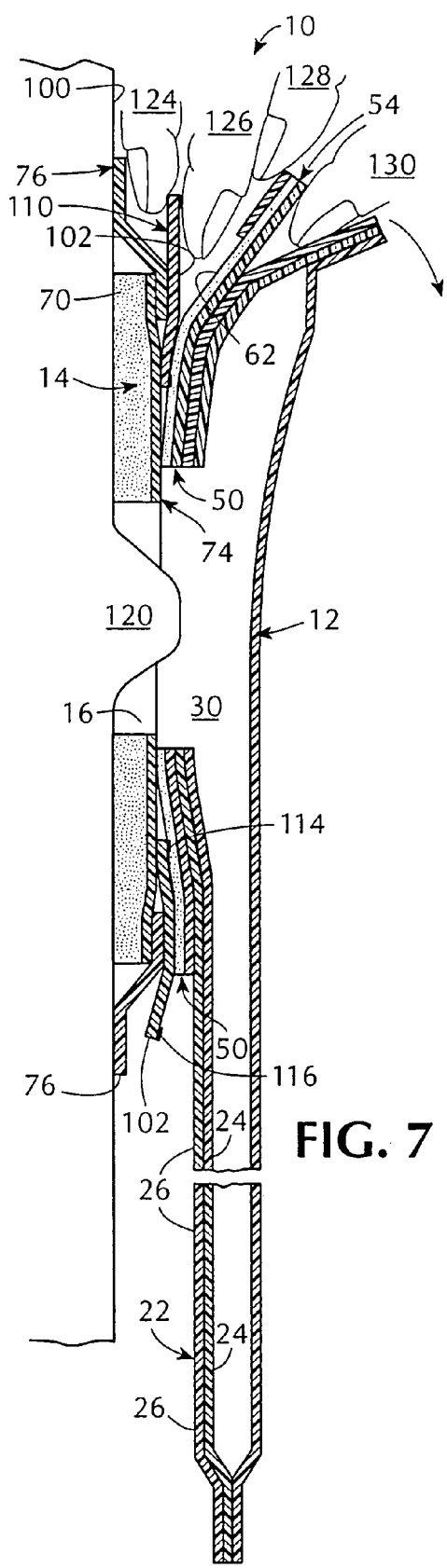
FIG. 6
FIG. 7

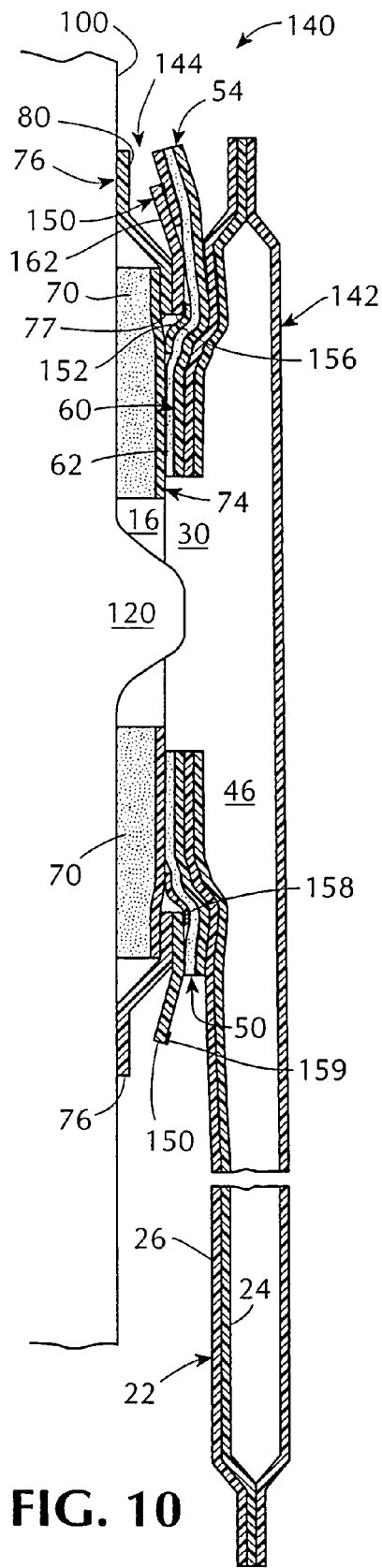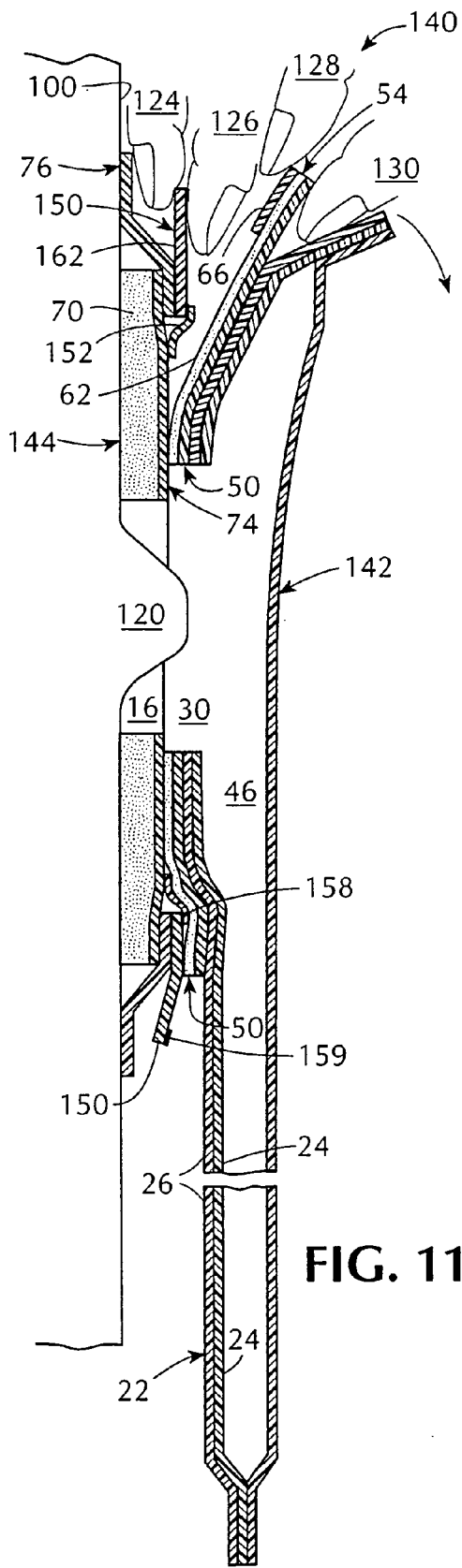
FIG. 10
FIG. 11

REPOSITIONABLE POUCH WITH FLOATING LANDING ZONE

CROSS REFERENCE

This patent application claims the benefit of U.S. Provisional Application Ser. No. 60/066,276, filed Nov. 20, 1997, which is incorporated by reference herein in its entirety.

BACKGROUND OF THE INVENTION

This invention is directed to ostomy systems wherein a pouch and a mounting wafer are adhesively coupled, and more particularly to an ostomy system wherein pouch peel-off or pull-away forces exerted on a mounting wafer during pouch separation from the mounting wafer can be substantially isolated from the abdominal area underlying the mounting wafer.

An adhesively coupled ostomy system such as shown in U.S. patent application Ser. No. 08/609,318 includes a pouch with a face plate that is adhesively secured to a body side mounting wafer. The ostomy system, because of a releasable and resealable adhesive coupling arrangement, permits repositioning of the pouch relative to the body side mounting wafer. Thus, once a pouch has been adhesively secured to a mounting wafer, the pouch can be removed and resecured as desired to obtain optimum positioning of the pouch on the mounting wafer.

To facilitate repositioning or removal of the pouch after it has been adhesively secured to a body side mounting wafer, a finger grippable tab is provided on the face plate of the pouch for gripping between the thumb and forefinger for example. During pouch removal when the pouch is gripped at the face plate tab the pull away or peeling force is directed through the tab and the face plate of the pouch thereby minimizing any stretching of the pouch envelope. Thus the pouch can be detached and repositioned on the mounting wafer for optimum adjustment.

However, the pull away force of the pouch is generally resisted at the mounting wafer and felt by the user at the underlying abdominal area. Since the underlying abdominal area is often sensitive to stress, the pull away or separation force of the pouch from the mounting wafer can be discomforting to the user.

It is thus desirable to provide an adhesively coupled ostomy system that enables the pouch pull away force from the mounting wafer to be isolated at the mounting wafer to minimize stressing the abdominal area underlying the mounting wafer.

OBJECTS AND SUMMARY OF THE INVENTION

Among the several objects of the invention may be noted the provision of a novel low profile adhesively coupled ostomy system wherein the pouch is repositionable, a novel low profile adhesively coupled ostomy system wherein the pouch face plate has an adhesive surface and the body side mounting wafer has a non-adhesive landing area surface, a novel low profile adhesively coupled ostomy system wherein a portion of the landing area surface of the mounting wafer is freely deflectable toward and away from the abdominal area when other portions of the landing area surface are immovable with respect to the abdominal area, a novel low profile adhesively coupled ostomy system wherein the body side mounting wafer, when joined to the abdominal area, has a landing area surface that is finger grippable, a novel low profile ostomy system including a pouch that adhesively attaches to a body side mounting wafer and wherein, the mounting wafer can be gripped when the pouch face plate is detached from the mounting wafer, and a novel method of separating an ostomy pouch from a mounting wafer to minimize stress and strain at the abdominal area underlying the mounting wafer.

Other objects and features of the invention will be in part apparent and in part pointed out hereinafter.

In accordance with the invention, the ostomy system includes a pouch, and a mounting wafer that are adhesively coupled, but are easily separable from each other, if desired, for repositioning of the pouch.

A manually accessible tab is provided on the face plate of the pouch and a finger grippable portion is provided on the mounting wafer. The finger grippable mounting wafer portion can thus be held while the pouch and face plate tab are peeled from or pulled away from the mounting wafer.

The adhesive coupling means for the ostomy system include a resealable adhesive and a releasable film, one of which is provided on the pouch face plate and the other of which is provided on the body side mounting wafer.

In a preferred embodiment of the invention the resealable adhesive is provided on the pouch face plate and the releasable film is provided on the body side mounting wafer.

The releasable film on the mounting wafer defines a landing zone for the adhesive face plate of the pouch. A first portion of the releasable film is immovable with respect to a body surface when the mounting wafer is secured to the body surface and a second portion of the releasable film is deflectable away from the body surface when the mounting wafer is secured to the body surface. The deflectable portion of the releasable film is sized to be finger grippable and is also referred to as the floating landing zone.

Easy-to-see indicia borderlines are provided for viewing at the landing zone to define a target area for the pouch face plate. The indicia borderlines also facilitate alignment of the pouch face plate with the mounting water.

The finger grippable portion of the mounting wafer permits the user to grip and hold the mounting wafer in order to exert a restraining force on the mounting wafer when the pouch is peeled or pulled away from the mounting wafer. The restraining force applied by the user on the mounting wafer can be made equal and opposite to the pouch peel off or pull away force in response to the user's sensation of stress or strain at the abdominal area underlying the mounting wafer.

Thus the floating landing zone portion of the mounting wafer can be gripped in a manner that helps to isolate the pouch peel off or pull away force from the abdominal area underlying the mounting wafer.

In two embodiments of the invention the releasable film landing zone on the mounting wafer is formed of two discrete sections of landing zone film. One landing zone section is larger than the other and overlays the smaller dimensional landing zone section.

In one embodiment of the invention the larger dimensional landing zone section directly contacts the smaller landing zone section and forms an extension of the smaller landing zone section. The larger landing zone section includes the floating landing zone.

In another embodiment of the invention the large dimensional landing zone section does not directly contact the smaller dimensional landing zone section. A transitional landing zone section is thus used to form a bridge between the large and small landing zone sections.

The invention also includes a method of separating an adhesively coupled pouch from a mounting wafer to permit repositioning of the pouch on the mounting wafer. The method also includes providing a landing surface formed of releasable film for the mounting wafer and rendering a portion of the landing surface deflectable toward and away from the body surface when the mounting wafer is secured to the body surface. The method further includes sizing the deflectable portion of the landing area to permit linger gripping of the deflectable portion when the pouch is pulled away from the mounting wafer during pouch separation.

The invention accordingly comprises the constructions and methods hereinafter described, the scope of the invention being indicated in the claims.

DESCRIPTION OF THE DRAWINGS

In the accompanying drawings,

FIG. 5 is an exploded perspective view of the body side mounting wafer thereof;

FIG. 6 is a sectional view of the ostomy system thereof positioned on the abdomen in alignment with a stoma;

FIG. 7 is a view similar to FIG. 6, showing the ostomy pouch being detached from the body side mounting wafer;

FIG. 10 is a sectional view of the mounting wafer thereof coupled with an ostomy pouch that is positioned on the abdomen in alignment with a stoma; and FIG. 11 is a view similar to FIG. 10 showing the ostomy pouch being detached from the body side mounting wafer.

Corresponding reference characters indicate corresponding parts throughout the several views of the drawings.

DETAILED DESCRIPTION OF THE INVENTION

An ostomy system incorporating one embodiment of the invention is generally indicated by the reference number 10.

Figure 1:
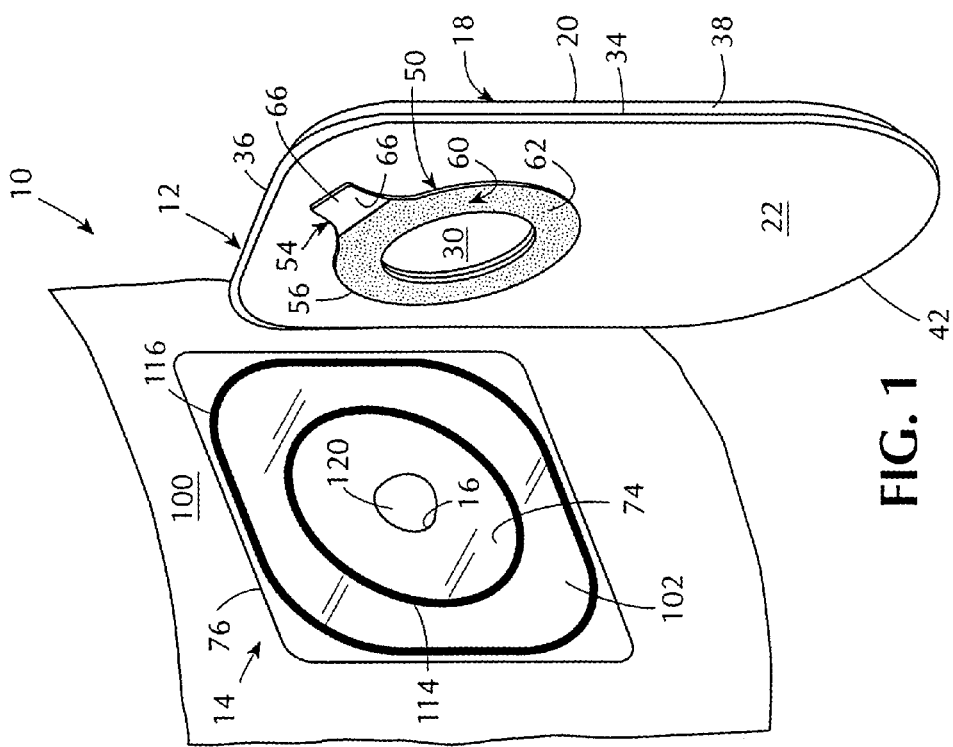
FIG. 1 is a simplified perspective view of an ostomy system incorporating one embodiment of the present invention, prior to adhesive attachment of the ostomy pouch to a body side mounting wafer.

Referring to FIG. 1, the ostomy system 10 includes a pouch 12 and a body-side mounting wafer 14 shown in separated position. The body-side mounting wafer 14 includes an opening 16 for a stoma 120 and is adhesively secured to an abdominal surface 100 in alignment with the stoma 120.

The ostomy pouch 12, which is expandable, is formed of a known envelope 18 of flexible thermoplastic material made in accordance with known techniques in the art of ostomy pouch construction. The pouch material is impermeable to gas and water.

Figure 2:
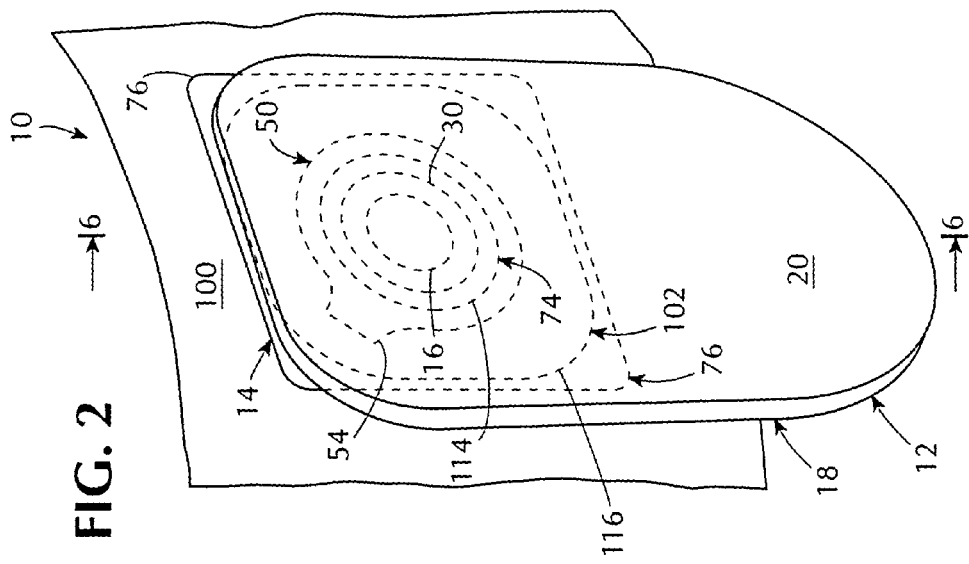
FIG. 2 is a simplified perspective view thereof after the ostomy pouch has been adhesively secured to the body side mounting wafer.

The pouch envelope 18 includes a front wall 20 (FIG. 2) that faces away from the abdominal surface 100 and a rear wall 22 (FIG. 1) that confronts the abdominal surface 100.

Referring to FIG. 6, the rear wall 22 of the pouch 12 includes an inside layer 24 of the same material as the front wall 20, and an outside layer 26 of perforated polyethylene flocking. The outside layer 26 provides a comfortable surface contact between the pouch 12 and the abdominal surface 100.

As seen in FIG. 6, both the layers 24 and 26 respectively include an aligned waste inlet opening 30. The front and rear walls 20 and 22 of the pouch 12 are joined together by a peripheral thermoweld 34 (FIGS. 1 and 6).

The pouch envelope 18 further includes a top portion 36 (FIG. 1) with rounded corners, opposite side portions 38 and 40 that are substantially parallel, and a curved bottom portion 42 that merges into the opposite side portions 38 and 40. The pouch envelope 18 thus defines a waste collection chamber 46 (FIG. 6) accessible through the waste inlet opening 30 of the rear wall 22.

The waste inlet opening 30 has a diameter of approximately 1¾ inches and is located nearer the top portion 36 of the pouch envelope than the bottom portion 42.

The pouch 12 further includes a generally annular adhesive face plate 50 that borders the waste inlet opening 30. The inner diameter of the face plate 50 aligns with the waste inlet opening 30 of the pouch 12 and is of substantially the same magnitude. For purposes of simplicity, the inner diameter of the face plate 50 is also referred to by the reference number 30. The face plate 50 is attached to the rear wall 22 of the pouch 12 by an annular thermoweld or by adhesion. The face plate 50 includes a manipulable tab 54 approximately one inch wide (FIG. 1) and extending approximately ½ inch beyond an outer diametrical periphery 56 of the face plate 50, at an angle of approximately 50° to 60° from the vertical. The surface portion of the face plate 50 between the inner and outer diameters 30 and 56 is referred to as the face plate adhesion area.

The face plate 50 is preferably formed of a resealable foam tape 60, such as the type manufactured by the 3M Company of Minneapolis, Minn. and designated No. 9776 Foam Medical Tape On Liner. The resealable foam tape 60 includes a closed cell polyethylene foam backing approximately 0.08 mm thick with a hypoallergenic pressure-sensitive acrylate adhesive 62 (FIG. 6) that is at the face plate adhesion area and a silicone release paper (not shown) that normally covers the adhesive 62. The face plate 50 has an inner diameter of approximately 1¾ inches, and an outer diameter of approximately 3⅜ inches.

The tab portion 54 of the face plate 50 includes a film layer 66 (FIG. 1) laminated to the acrylic adhesive 62 of the tab 54. Preferably the film layer 66 is plasticized, flexible polyvinylchloride sheet material approximately 0.010 to 0.080 inches thick, with an outside surface that is non-adhesive to facilitate manipulation of the tab portion 54 and to reinforce the tab 54 when it is manually gripped between the fingers as shown in FIG. 7.

As most clearly shown in FIG. 6, a rear surface 68 of the tab portion 54 that confronts the rear wall 22 of the pouch 16 is non-adhesive and is not joined to the pouch wall 22 to further ensure that the tab portion 54 is accessible for manual gripping and manipulation.

Manipulation or gripping of the tab 54 enables the user to peel the pouch face plate 50 from the mounting wafer 14 during pouch removal or pouch separation as shown in FIG. 7. During removal of the pouch face plate 50 from the body side mounting wafer 14 the peeling force is directed through the tab 54 and the face plate area, rather than the walls 20 and 22 of the pouch 12.

Referring to FIGS. 3-6 the body-side mounting wafer 14 is a laminate of generally circular and rectangular layers. The mounting wafer 14 has a central opening 16 with a diameter of approximately ¾ to 1¼ inches.

Figure 4:
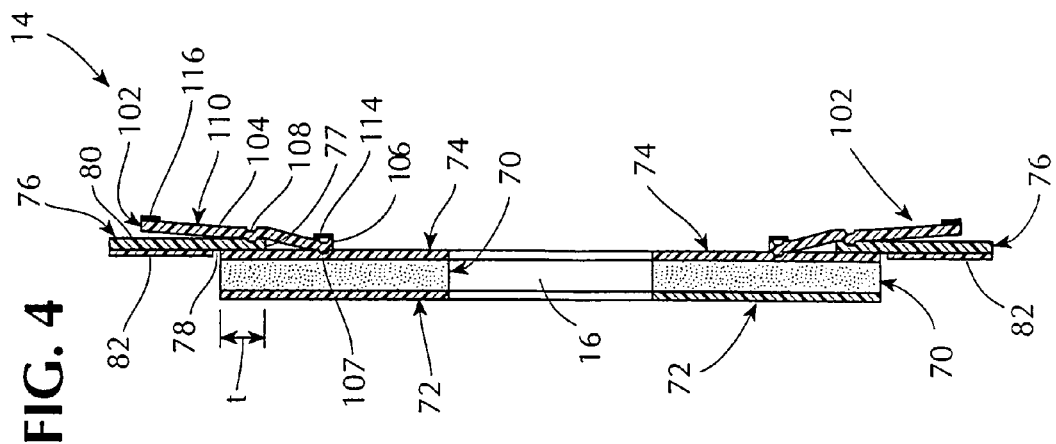
FIG. 4 is a sectional view thereof taken on the line 4-4 of FIG. 3.
Figure 3:
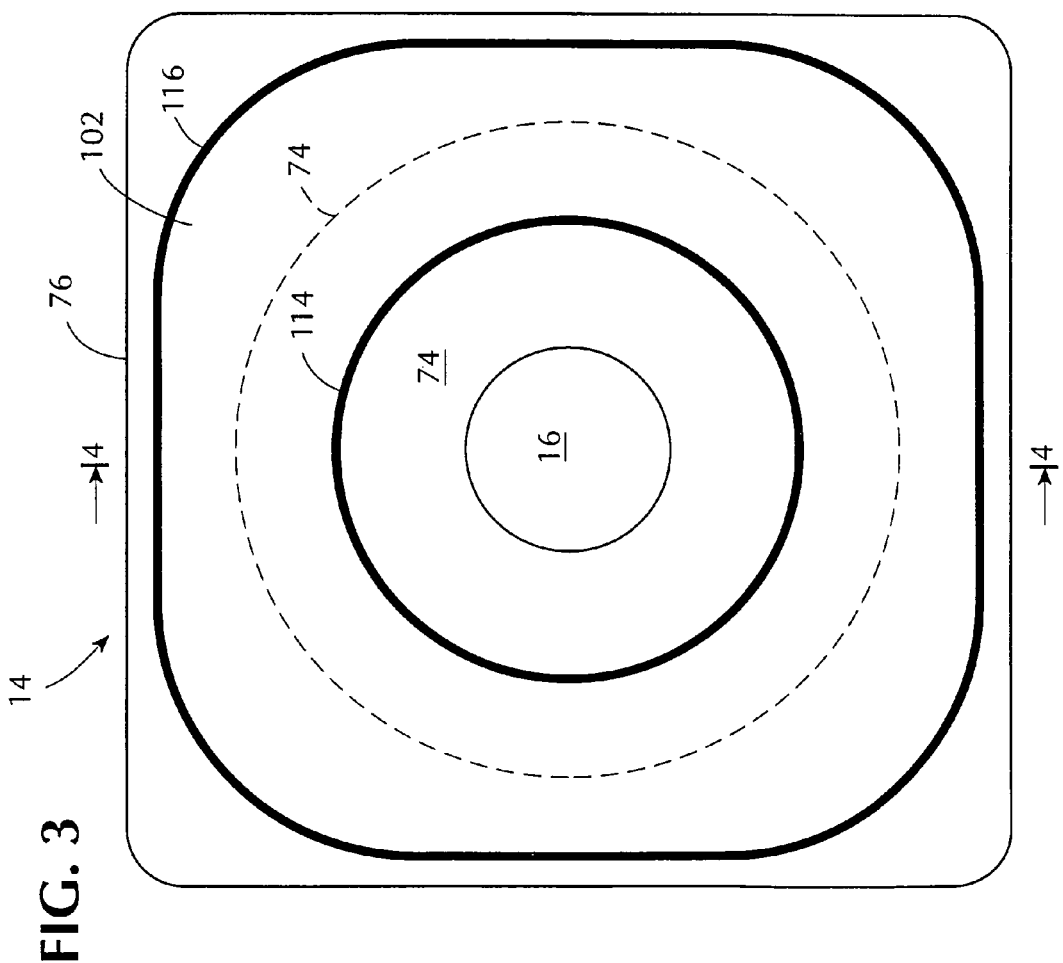
FIG. 3 is a plan view of the body side mounting wafer thereof.

Referring to FIGS. 4 and 5, the body-side mounting wafer 14 includes an annular adhesive disc 70 for abdominal contact. The disc 70 is covered on one side with a removable layer 72 of silicone release paper and on the other side with a non-removable layer 74 of plastic film also referred to as the first landing zone film layer, preferably formed of polyethylene film. The layers 72 and 74 are substantially identical in inner and outer diameter to the abdominal adhesive disc 70. The abdominal adhesive disc 70 is preferably formed of a hydrocolloid adhesive, approximately 0.030 to 0.080 inches thick, such as the type sold under the trademark Stomahesive® or Durahesive® by Bristol-Myers Squibb Company of New York, N.Y.

The body-side mounting wafer 14 further includes a generally rectangular fabric collar 76 having an inner diameter 77. The fabric collar 76 is preferably formed of Fasson material having an adhesive coating 78 (FIG. 5) facing the first landing zone film layer 74 and a soft, perforated non-adhesive back surface 80. A silicone release collar 82 for the adhesive side 78 of the collar 76 has preformed cut lines 84 and 86 (FIG. 5) that define opposite manipulation segments 88 and 90 and a median section 92. For purposes of simplicity the reference numbers 88, 90 and 92 are also used to define the corresponding underlying adhesive segments and sections on the surface 78 of the fabric collar 76. Under this arrangement, an annular portion "t" (FIG. 4) of the adhesive side 78 of the fabric collar 76 bonds to the polyethylene film layer 74.

Referring to FIGS. 4 and 5, a generally rectangular layer 102 of plastic film, also referred to as the second landing zone film layer, is joined to the first landing zone film layer 74 and the fabric collar 76. The layer 102 is preferably formed of polyethylene and can be of the type manufactured by the 3M Company of Minneapolis, Minn. under the designation 3M MSX-1198 Clear PE Release Film.

The second landing zone film layer 102 is approximately 12 mils in thickness, has an inner diameter 106 of approximately 1½ inches and a width across flats of approximately 3¾ inches. An exposed landing surface 104 is defined between the inner diameter 106 and the outer periphery of the layer 102. A darkened, easy-to-see indicia border 114 is provided on the layer 102 proximate the inner diameter 106 and another darkened easy to-see indicia border 116 is provided on the layer 102 proximate its outer periphery. The indicia borders 114 and 116 are preferably provided on the back of the layer 102 but are shown in the drawings on the landing surface 104 for purposes of clarity.

The second landing zone film layer 102 is joined at or near its inner diameter 106 to the film layer 74 by an annular ultrasonic weld 107 having an inner diameter of approximately 1½ inches and an outer diameter of approximately 1¾ inches. The second landing zone film layer 102 is further joined to the fabric collar 76 at or near the inner diameter 77 of the fabric collar 76 by an annular ultrasonic weld 108 having an inner diameter of approximately 2⅛ inches and an outer diameter of approximately 2⅜ inches.

Under this arrangement the second landing zone film layer 102 forms a radial extension of the landing surface provided by the first landing zone film layer 74. A portion of the second landing zone film layer 102 that extends radically beyond the ultrasonic weld 108 is free from securement to the fabric collar 76 and is thus referred to as the floating landing zone 110.

As most clearly shown in FIG. 4, the mounting wafer 14, as assembled for securement to the abdominal surface 100, includes the adhesive layer 70 sandwiched between the silicone release paper 72 and the first landing zone film layer 74. The assembled body-side mounting wafer 14 also includes the fabric collar 76 secured to a peripheral section of the first landing zone film layer 74. The fabric collar 76 extends radially beyond the periphery of the first landing zone film layer 74. The adhesive surface 92 of the fabric collar 76 that extends radially beyond the first landing zone film layer 74 is covered by the silicone release paper 82.

The assembled mounting wafer 14 further includes the second landing zone film layer 102 secured to the first landing zone film layer 74 and the fabric collar 76 as previously described.

In using the ostomy system 10, the body-side mounting wafer 14 is first joined to the abdominal surface 100 before being coupled with the pouch 12. Thus, the silicone release paper 72 is removed from the abdominal adhesive disc 70 and the median section 92 of the release paper 82 is removed from the fabric collar 76. The release paper 82 temporarily remains at the opposite manipulation edge portions 88 and 90 of the fabric collar 76. The mounting wafer 14 can then be handled by the manipulation portions 88 and 90, to locate the body-side mounting wafer opening 16 in alignment with the stoma 120. The body-side mounting wafer 14 is secured to the abdominal surface 100 by the adhesive disc 70 and the exposed median section 92 of the fabric collar 76. The remaining release paper 82 at the manipulation sections 88 and 90 is then removed to expose the underlying adhesive and complete the securement of the fabric collar 76 to the abdominal surface 100. The portion of the fabric collar 76 that projects beyond the periphery of the mounting wafer components 70, and 84 thus attaches to the abdominal surface 100 and thereby covers the peripheral edges of the abdominal adhesive disc 70 and the first landing zone film layer 74.

With the body-side mounting wafer 14 secured to the abdominal surface 100, the pouch 12 can then be secured to the body-side mounting wafer 14. Silicone release paper (not shown) protecting the annular face plate 50 of the pouch 12 is removed to expose the adhesive surface 62. The face plate 50 can be grasped at the tab portion 54 to facilitate manipulation of the face plate 50 against the first and second landing zone film layers 74 and 102 of the body-side mounting wafer 14. The tab portion 54 facilitates alignment of the pouch waste inlet opening 30 with the mounting wafer 14 and the stoma 120. In addition, the easy-to-see indicia borders 114 and 116 (FIGS. 1, 3 and 5) at the inner and outer edges of the second landing zone film 102 facilitate such alignment.

Figure 8:
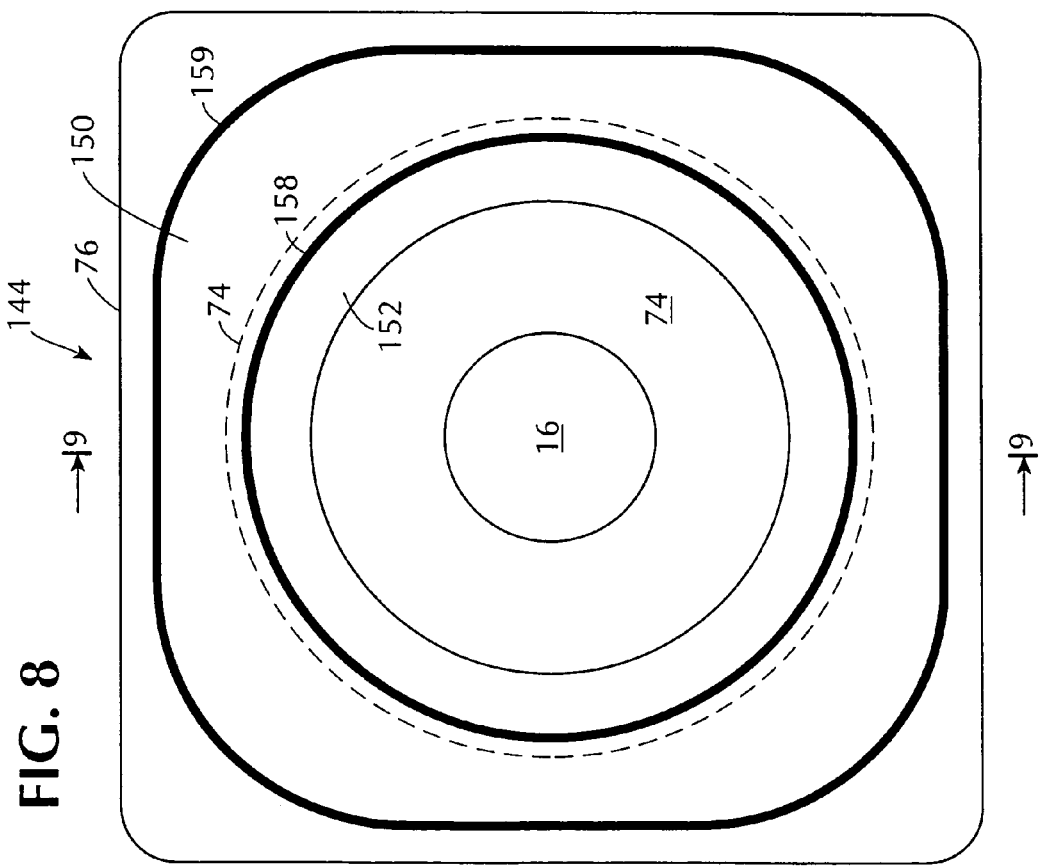
FIG. 8 is plan view of a body side mounting wafer incorporating another embodiment of the invention.

Once the pouch 12 is secured via the faceplate 50 to the mounting wafer 14, it may be desirable to adjust or reposition the pouch 12 against the mounting wafer 14. The tab portion 54 of the face plate 50 is accessible for manual grasping, as shown in FIG. 8, to peel the annular face plate 50 from the releasable first and second landing zone film layers 74 and 102 of the body-side mounting wafer 14. The releasable qualities of the film layers 74 and 102 facilitate removal of the pouch face plate 50 from the mounting wafer 14.

The pouch pull-off or peeling force at the pouch face plate 50 is exerted upon the mounting wafer 14 and the underlying abdominal area. Because the underlying abdominal area can be sensitive to the stress and strain of pouch removal it is desirable to minimize such stress and strain at the abdominal area. The pouch peel off force can be substantially isolated from the abdominal area underlying the mounting wafer 14 by gripping the unbonded or floating landing zone portion 110 of the second landing zone layer 102 during the peel off process.

Gripping of the mounting wafer 14 at the floating landing zone 110 by the fingers 124 and 126 helps to provide a force on the mounting wafer 14 that is equal and opposite to the pouch peel off force provided by the fingers 128 and 130 that grip the face plate tab 54. Thus if the user begins to feel any stress or strain at the abdominal area during pouch peel off, the user can either increase or decrease the restraining force applied to the mounting wafer 14.

The user can also manipulate the floating landing zone portion 110 to vary the direction of the restraining force, as needed to counteract the pouch peel off force. In this manner, the underlying abdominal area is substantially isolated from the pouch peel off force. Thus stress and strain on the underlying abdominal area during pouch peel off can be substantially minimized.

Resecurement of the annular face plate 50 to the first and second landing zone areas 74 and 102 of the body-side mounting wafer 14 is then accomplished in a manner similar to that previously described. The resealable qualities of the adhesive surface 62 facilitate resecurement of the face plate 50 to the mounting wafer 14.

Figure 9:
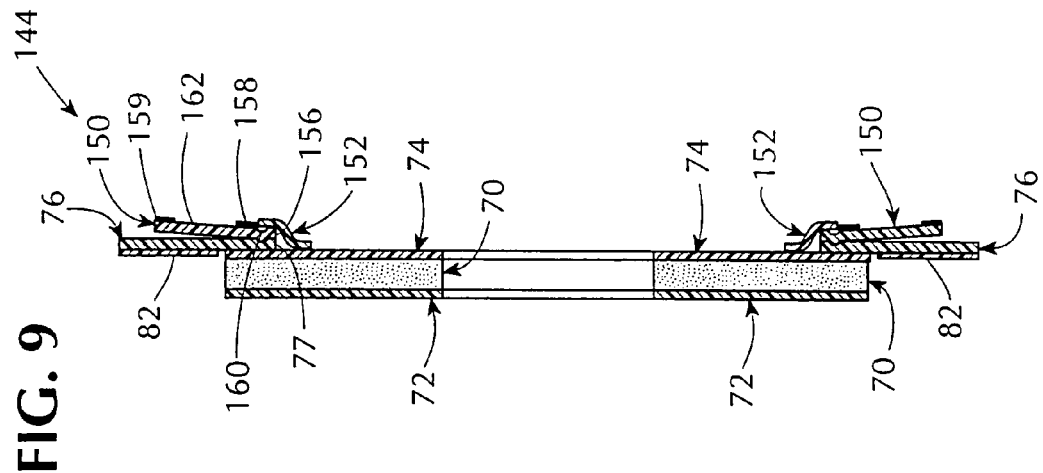
FIG. 9 is a sectional view thereof, taken on the line 9-9 of FIG. 8.

Another embodiment of the ostomy system is generally indicated by the reference number 140 in FIGS. 10 and 11. The ostomy system 140 includes a pouch 142 identical to the pouch 12 and a mounting wafer 144. The mounting wafer 144 (FIGS. 8 and 9) includes the adhesive disc 70 sandwiched between the silicone release paper 72 and the first landing zone film layer 74, the fabric collar 76 adhered to the first landing zone film layer 74, the silicone release collar 82 with a second landing zone film layer 150 joined to the fabric collar 76, and a security film 152 joined to the first and second landing zone film layers 74 and 150.

The second landing zone film layer 150 is formed of the same material as the second landing zone film layer 102 of the mounting wafer 14 and is also of generally rectangular shape with a width across flats of approximately 3¾ inches by 3¾ inches. The second landing zone film layer 150 differs from the corresponding layer 102 of the mounting wafer 14 by having a thickness of approximately 18 mils and an inner diameter 156 that aligns with and is of the same magnitude as the inner diameter 77 of the fabric collar 76.

Easy-to-see indicia borders 158 and 159 are respectively provided proximate the inner diameter 156 and the outer periphery of the second landing zone film layer 150 for the same purpose as the indicia borders 114 and 116 on the mounting wafer 14.

The second landing zone film layer 150 is joined at or near its inner diameter 156 to the film layer 74 by an annular ultrasonic weld 160 (FIG. 9) having an inner diameter of approximately 2⅛ inches and an outer diameter of approximately 2⅜ inches. Under this arrangement the second landing zone film layer 150 forms a radial extension of the landing surface provided by the first landing zone film layer 74. A portion 162 of the second landing zone film layer 150 that extends radially beyond the ultrasonic weld 160 is free from securement to the fabric collar 76 and thus referred to as the floating landing zone 162.

The security film 152 is a ring of plastic material, preferably formed of the same material as the first landing zone film layer 74. The security film 152 has a thickness of approximately 2 mils with an inner diameter approximately 1¾ inches and an outer diameter of approximately 2⅜ inches. Ultrasonic welds (not shown) provided at or near the inner and outer diameters of the security film 152 join the security film 152 to the first and second landing zone film layers 74 and 150 such that the security film 152 covers the inner diametrical edges 77 and 156 of the fabric collar 76 and the second landing zone film layer 150. The security film 152 thus provides a transitional landing surface between the first and second landing zone film layers 74 and 150.

In using the ostomy system 140, the body side mounting wafer 144 is joined to the abdominal surface 100 and the pouch 12 is joined to the mounting wafer 144 in a manner similar to that previously described for the ostomy system 110.

Referring to FIG. 10, the adhesive surface 62 of the pouch face plate 50 contacts the first and second landing zone film layers 74 and 150 and the security film 152, which provide a releasable surface for the resealable adhesive 62 of the pouch face plate 50.

Peel off or pull away of the pouch face plate 50 from the mounting wafer 144 is accomplished in a manner similar to that described for the ostomy system 10. Thus the face plate 50 is grasped at the tab portion 54 and the mounting wafer 144 is grasped at the floating landing zone 162 as shown in FIG. 11. In this manner, and as described with respect to the ostomy system 10, gripping of the mounting wafer 144 at the floating landing zone 162 by the fingers 124 and 126 help to provide a restraining force on the mounting wafer 144 that is equal and opposite to the pouch peel off force provided by the fingers 128 and 130 on the face plate tab 54.

Some advantages of the present invention evident from the foregoing description include a low profile repositionable ostomy system with a mounting wafer that has a floating landing zone. A further advantage is a manipulable tab portion of the pouch face plate and a manipulable portion of the body-side mounting wafer are manually grippable during pouch removal to help isolate pouch peel off force from the abdominal area underlying the mounting wafer. A further advantage is the provision of indicia borders on the mounting wafer to facilitate alignment of the pouch face plate on the mounting wafer.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An ostomy system comprising:
   a) an ostomy pouch including a pouch envelope formed of flexible plastic material defining a waste collection chamber for body waste that passes through a stoma, a waste inlet opening formed in said envelope for positioning around said stoma to permit passage of waste material from said stoma to said collection chamber, flexible annular adhesive pouch coupling means on said envelope at said waste inlet opening for adhesively coupling said ostomy pouch with a body side mounting wafer, said pouch coupling means including an integral projection extending therefrom having a top and bottom surface for manually gripping and manipulating said pouch coupling means by the thumb and forefinger of a first hand, said bottom surface being non-adhesive,
   b) non-adhesive rendering and reinforcing means for rendering said top surface of said projection non-adhesive and reinforcing said projection to facilitate gripping and manipulating said pouch coupling means, and
   c) a body-side mounting wafer joinable to a body surface around a stoma, said body side mounting wafer having an opening for a stoma and a non-adhesive landing area surface on a front side of the mounting wafer for coupling engagement with said adhesive portion of said pouch coupling means, said landing area surface having indicia for delineating locations thereon, said integral projection manipulation and landing surface indicia facilitating alignment of the waste inlet opening of the pouch and stoma opening of the body-side mounting wafer, said non-adhesive landing area having a substantially rectangular shape and including a first portion that is immovable with respect to said mounting wafer, and a second portion having a substantially rectangular periphery that is flexible throughout and composed of a thin single component film layer, said second portion being deflectable away from said body surface and predeterminedly dimensioned so as to permit and facilitate manual gripping and manipulation of said second portion by the thumb and forefinger of a second hand, said second portion having a substantially rectangular periphery and also being predeterminedly dimensioned to have a section at least partly surrounding the annular adhesive pouch coupling means during adhesive coupling that is unbonded, said non-adhesive integral projection and unbonded section being predeterminedly dimensioned to extend adequately to permit and facilitate manually gripping of both simultaneously and manipulation of both simultaneously by the thumbs and forefingers of both hands for facilitating peeling said ostomy pouch and mounting wafer apart and minimizing stress to the body surface around the stoma.

2. The ostomy system as claimed in claim 1, wherein said second portion has a peripheral edge with a predetermined periphery and substantively the entire periphery of said non-adhesive landing area at said peripheral edge is deflectable away from said body surface.

3. The ostomy system as claimed in claim 2, wherein said predetermined periphery is generally rectangular with rounded corners and the deflectable second portion of said non-adhesive landing area extends inwardly from said peripheral edge to a generally circular boundary within the confines of said peripheral edge.

4. The ostomy system as claimed in claim 1, wherein said non-adhesive landing area includes first and second discrete sections, each having inner and outer peripheries, and said first and second discrete sections are sized such that said first section overlays the outer periphery of said second section, and the exposed first peripheral edge is at the outer periphery of said first section.

5. The ostomy system as claimed in claim 2, wherein a first indicia borderline is provided for viewing at said non-adhesive landing area proximate said peripheral edge.

6. The ostomy system as claimed in claim 5, wherein the inner periphery of said second discrete section is of a lesser magnitude than the inner periphery of said first section and a second indicia borderline is provided for viewing at said non-adhesive landing area between the inner periphery of said second section and the outer periphery of said first section.

7. The ostomy system as claimed in claim 6, wherein the second indicia borderline is provided for viewing as said non-adhesive landing area proximate the inner periphery of said first section.

8. The ostomy system as claimed in claim 4, wherein an intermediate annular section overlays a first portion of said first section and a second portion of said second section of said non-adhesive landing area.

9. The ostomy system as claimed in claim 8, wherein said intermediate annular section has an exposed non-adhesive surface that constitutes a portion of said non-adhesive landing area surface.

10. The ostomy system as claimed in claim 4, wherein said second section of said non-adhesive landing area extends radially beyond said first section of said non-adhesive landing area and said mounting wafer further includes a fabric portion sandwiched between the first and second sections of said non-adhesive landing area, said fabric portion extending radially beyond said first and second sections of said non-adhesive landing area.

11. The ostomy system as claimed in claim 10, wherein said deflectable second portion of said non-adhesive landing area confronts said fabric portion.

12. The ostomy system as claimed in claim 11, wherein said fabric portion has an outer periphery that extends beyond the exposed first peripheral edge of said non-adhesive landing area.

13. The ostomy system as claimed in claim 1, wherein said non-adhesive rendering and reinforcing means includes a film layer on said top surface of said projection.

14. The ostomy system as claimed in claim 1, wherein said projection includes a central layer of polyethylene foam with a film layer on said top surface and a bottom surface that is non-adhesive.

* * * * *